US011918493B2

(12) United States Patent
Caldwell et al.

(10) Patent No.: US 11,918,493 B2
(45) Date of Patent: Mar. 5, 2024

(54) PROSTHETIC LINER APPARATUS FOR IMPROVED SUSPENSION

(71) Applicant: Northwestern University, Evanston, IL (US)

(72) Inventors: Ryan J. Caldwell, Long Grove, IL (US); Stefania Fatone, Chicago, IL (US)

(73) Assignee: Northwestern University, Evanston, IL (US)

( * ) Notice: Subject to any disclaimer, the term of this patent is extended or adjusted under 35 U.S.C. 154(b) by 382 days.

(21) Appl. No.: 17/292,053

(22) PCT Filed: Nov. 8, 2019

(86) PCT No.: PCT/US2019/060475
§ 371 (c)(1),
(2) Date: May 7, 2021

(87) PCT Pub. No.: WO2020/106474
PCT Pub. Date: May 28, 2020

(65) Prior Publication Data
US 2021/0393420 A1    Dec. 23, 2021

Related U.S. Application Data

(60) Provisional application No. 62/757,820, filed on Nov. 9, 2018.

(51) Int. Cl.
*A61F 2/78* (2006.01)
*A61F 2/80* (2006.01)
*A61F 2/50* (2006.01)

(52) U.S. Cl.
CPC .............. *A61F 2/7812* (2013.01); *A61F 2/80* (2013.01); *A61F 2002/5009* (2013.01); *A61F 2002/7818* (2013.01); *A61F 2002/802* (2013.01)

(58) Field of Classification Search
CPC .. A61F 2/7812; A61F 2/80; A61F 2002/5009; A61F 2002/7818; A61F 2002/802
See application file for complete search history.

(56) References Cited

U.S. PATENT DOCUMENTS

2005/0267598 A1   12/2005   Bjarnason et al.
2015/0052993 A1    2/2015   Batzdorff
(Continued)

FOREIGN PATENT DOCUMENTS

EP    2353550 A1    8/2011

OTHER PUBLICATIONS

May 6, 2020—(WO) International Search Report and Written Opinion—App PCT/US2019/060475.

*Primary Examiner* — Bruce E Snow
(74) *Attorney, Agent, or Firm* — Banner & Witcoff, Ltd.

(57) ABSTRACT

Prosthetic liner apparatus for improving suspension and rotation control between a residual limb and a socket of a prosthesis include a liner body having a shape configured to receive the residual limb and having an outer surface that fits within the socket. The liner body may have a plurality of raised elastomeric grips located on its outer surface and a proximal end of the outer surface of the liner body includes at least an exposed smooth elastomeric region that fits within and seals with the socket. Further disclosed is a prosthetic sock having raised elastomeric grips on its inner and outer surfaces which is for use with a liner body that is smooth or textured and that may or may not include raised elastomeric grips, and that when used together with the liner body ay form a liner apparatus.

20 Claims, 7 Drawing Sheets

(56) References Cited

U.S. PATENT DOCUMENTS

2015/0105866 A1    4/2015  Mackenzie
2017/0105853 A1*  4/2017  Jonsson .................... A61F 2/80
2017/0304085 A1    10/2017  Kurth
2017/0367854 A1*  12/2017  King ......................... A61F 2/80

* cited by examiner

ND SUSPENSION

CROSS-REFERENCE TO RELATED APPLICATIONS

This application claims priority to U.S. Provisional Patent Application No. 62/757,820, titled "Prosthetic Liner Apparatus For Improved Suspension" and filed Nov. 9, 2018, the disclosure of which is hereby incorporated by reference in its entirety.

CONTRACTUAL ORIGIN OF THE INVENTION

This invention was made with government support under W81XWH-10-1-0744 awarded by the US Army Medical Research and Materiel Command (Army/MRMC). The government has certain rights in the invention.

BACKGROUND

The present disclosure generally relates to suspension systems for prosthetic devices, and more particularly to liners for use in suction suspension systems for prosthetic limbs.

Various systems have been developed for coupling a prosthesis, in the form of a prosthetic device or prosthetic limb, to a residual limb of an amputee. The residual limb is connected to the prosthesis via a socket which receives and holds in place an end portion of the residual limb. Suspension is the mechanism that holds the socket to the residual limb. Suction is a form of suspension that uses a difference in atmospheric pressure to hold a socket to the residual limb. In turn, two approaches may be used to provide the suction, including passive suction and active vacuum. Liners help protect the residual limb tissue by providing cushioning and helping distribute the applied negative pressure in a uniform manner, while providing additional suspension force in the form of passive suction and adherence to the skin.

Modern prosthetic sockets for above-the-knee (transfemoral) and below-the-knee (transtibial) amputees typically incorporate an elastomeric liner to provide cushioning and facilitate suspension of the prosthesis. Persons with limb amputation may experience pistoning, slipping, and/or rotation of the socket relative to the residual limb, resulting in inadequate control of the prosthetic limb.

Foundational to successful prosthetic socket fittings, are liners with characteristics that address difficult residual limb shapes, poor tissue coverage, and durability. Liners may incorporate a sealing membrane on the external surface of the liner that can limit proportionally how much of the residual limb is subject to suspension forces. Generally speaking, the greater the surface area of the liner subjected to suspension forces within the socket, the more secure the prosthesis will feel in relation to the residual limb. However, currently available liners with sealing systems typically seal at the most distal location where a seal occurs, which greatly reduces the amount of surface area that may be subject to suction suspension, whether applied as passive suction or active vacuum. This disadvantageously increases the likelihood and extent of movement between the socket and the residual limb.

The present disclosure addresses shortcomings in prior art vacuum suspension systems for prosthetic limbs, without need to modify the socket, while providing improved suspension and rotation control of prosthetic limbs.

SUMMARY OF THE DISCLOSURE

The purpose and advantages of the disclosure will be set forth in and apparent from the description and drawings that follow, as well as will be learned by practice of the claimed subject matter.

The present disclosure generally provides improved liner apparatus for use with suction suspended prosthetic limbs, and is particularly useful for transfemoral and transtibial amputees. The ability to avoid undesirable movement between a socket of a prosthesis and an amputee's residual limb advantageously improves comfort and avoids soft tissue damage.

The present disclosure provides liner apparatus that can reduce rotation and improve suspension in both passive suction and active vacuum suspension systems. Thus, the improved liners are beneficial whether using a passive suction suspension system, which may simply include inserting a residual limb into a socket having a one-way valve, or using an active vacuum suspension system, which may use a source of vacuum, such as a mechanical and/or electrical pump, to remove air from the socket of the prosthesis.

Accordingly, in a first example aspect, disclosed herein is a prosthetic liner apparatus for improving suspension and rotation control between a residual limb and a socket of a prosthesis, including a liner body having a shape configured to receive the residual limb and having an outer surface that fits within the socket. A plurality of intermittent and incomplete raised elastomeric grips are located on the outer surface of the liner body, wherein at a proximal end of the liner body, the outer surface of the liner body includes at least an exposed smooth elastomeric region that fits within and seals with the socket, and wherein when the socket is subjected to passive suction or active vacuum, the raised elastomeric grips are held securely against the socket while the exposed smooth elastomeric region at the proximal end of the liner body seals to the socket.

In a second example aspect, disclosed herein is a prosthetic liner apparatus for improving suspension and rotation control between a residual limb and a socket of a prosthesis, including a liner body having a shape configured to receive the residual limb and having an outer surface that fits within the socket. The prosthetic liner apparatus further comprises a prosthetic sock having a textile sock portion having inner and outer surfaces covered by an elastomeric membrane and being configured to receive the liner body and to have the outer surface of the prosthetic sock fit within the socket, and having a plurality of intermittent and incomplete raised elastomeric grips located on the elastomeric membrane that covers the inner and outer surfaces of the textile sock portion, so as to extend inward and outward from the prosthetic sock, wherein when the socket is subjected to passive suction or active vacuum, the raised elastomeric grips are held securely against the socket.

In another example aspect, disclosed herein is a prosthetic liner apparatus for improving suspension and rotation control between a residual limb and a socket of a prosthesis, including a liner body having a shape configured to receive the residual limb and having an outer surface that fits within the socket. A plurality of intermittent and incomplete raised elastomeric grips are located on the outer surface of the liner body, wherein at a proximal end of the liner body, the outer surface of the liner body includes at least an exposed smooth elastomeric region that fits within and seals with the socket.

It will be appreciated that the liner apparatus for engagement between a residual limb and a socket of a prosthesis of this disclosure may have various configurations and the appended claims are not to be limited to the examples illustrated. Thus, the present disclosure presents alternatives to prior art liner apparatus and prior methods of engagement between a residual limb and a socket of a prosthesis.

It is to be understood that both the foregoing general description and the following detailed description are exemplary and provided for purposes of explanation only, and are not restrictive of the subject matter claimed. Further features and objects of the present disclosure will become more fully apparent in the following description of the preferred embodiments and from the appended claims.

BRIEF DESCRIPTION OF THE FIGURES

In describing the preferred embodiments, reference is made to the accompanying figures wherein like parts have like reference numerals, and wherein:

FIG. 1A depicts a standard liner worn between a residual limb and a socket. FIG. 1B depicts a prosthetic sock with internal and external raised grips worn between a liner and a socket. FIG. 1C depicts a liner with external raised grips between a residual limb and a socket. FIG. 1D depicts a prosthetic sock with internal and external raised grips worn between a liner and a socket. In all cases, FIGS. 1A through 1D, the exterior surface of the liner may be smooth or have textile texture. Moreover, the examples of FIGS. 1A through 1D are depicted in a transtibial application, but can be also used with transfemoral applications. The internal and external raised grips may be continuous or discontinuous.

It should be understood that the figures are not to scale. The figures provide some details of a liner apparatus for improving suspension and rotation control with a socket of a prosthesis, including different plane and section views of the liner apparatus examples. Additional details are considered well within the comprehension of those of skill in the art in light of the present disclosure. It also should be understood that the present disclosure is not limited to the example embodiments illustrated.

DETAILED DESCRIPTION OF THE PREFERRED EMBODIMENTS

Referring generally to FIGS. 1A-7, it will be appreciated that a prosthetic liner apparatus for improving suspension and rotation control between a residual limb and a socket of a prosthesis of the present disclosure generally may be embodied within numerous configurations.

Figure 1:
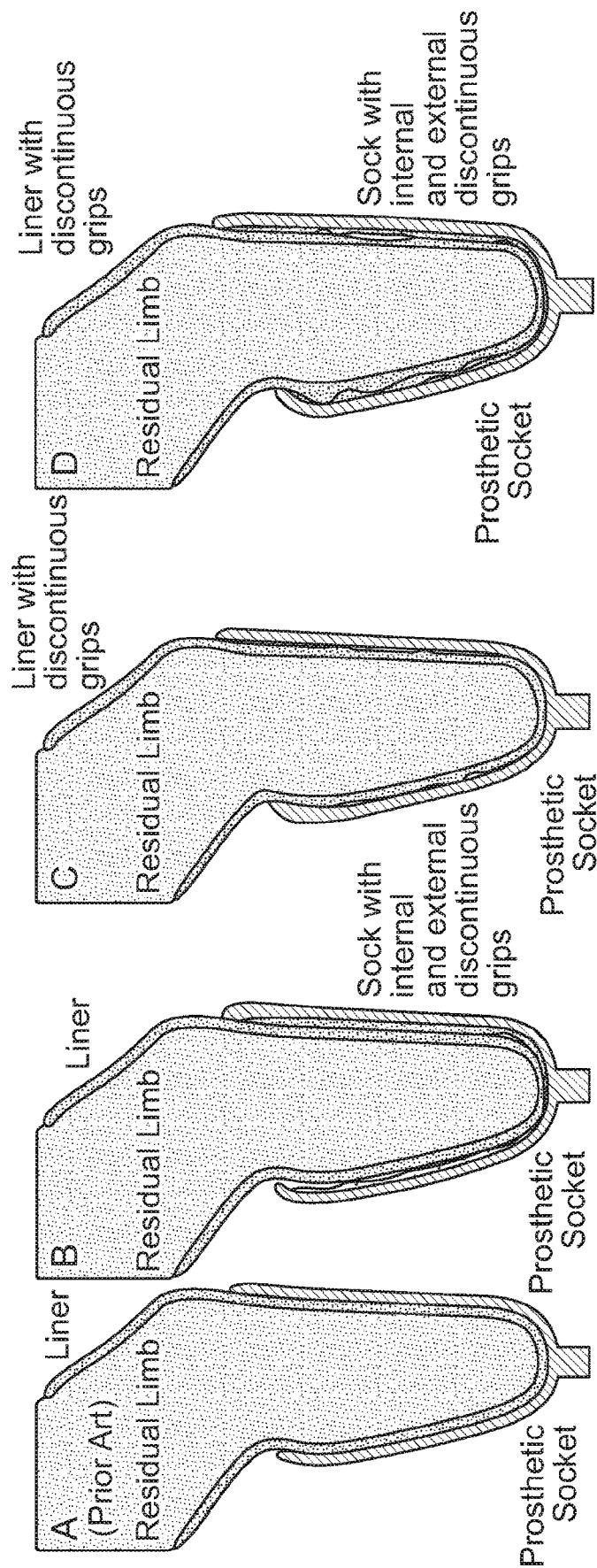
FIGS. 1A-1D are series of simplified cross-sectional views of examples.
Figure 2:
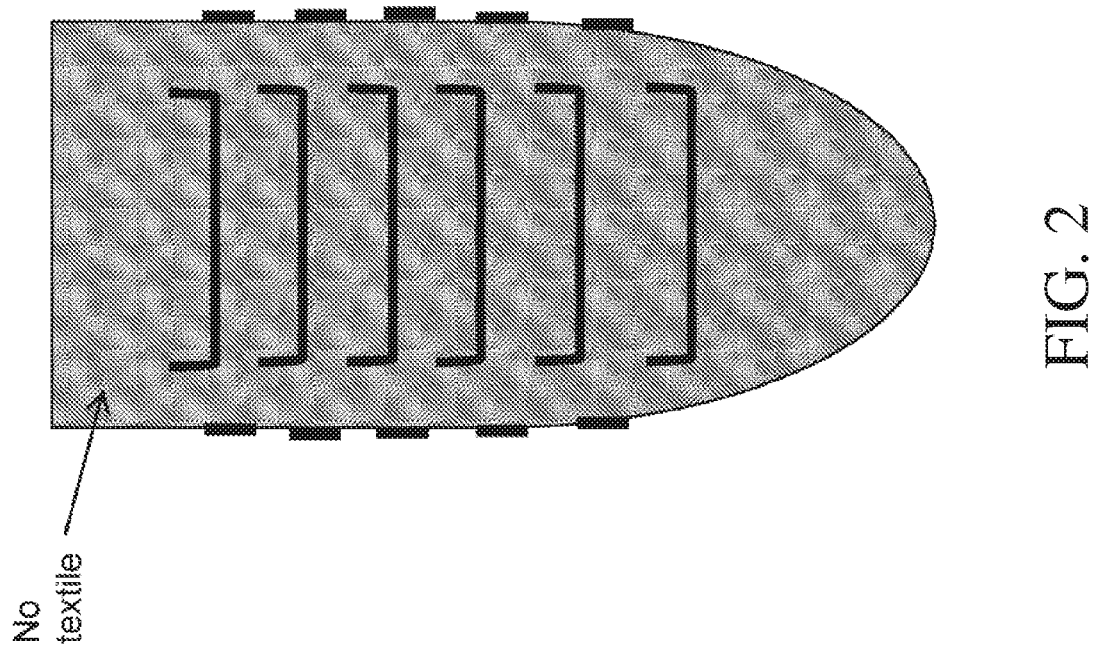
FIG. 2 provides a simplified front view of a first version of the liner apparatus shown in FIG. 1C having a smooth, uncovered outer surface and raised grips in alternating patterns incorporated into the mold of the liner.
Figure 3:
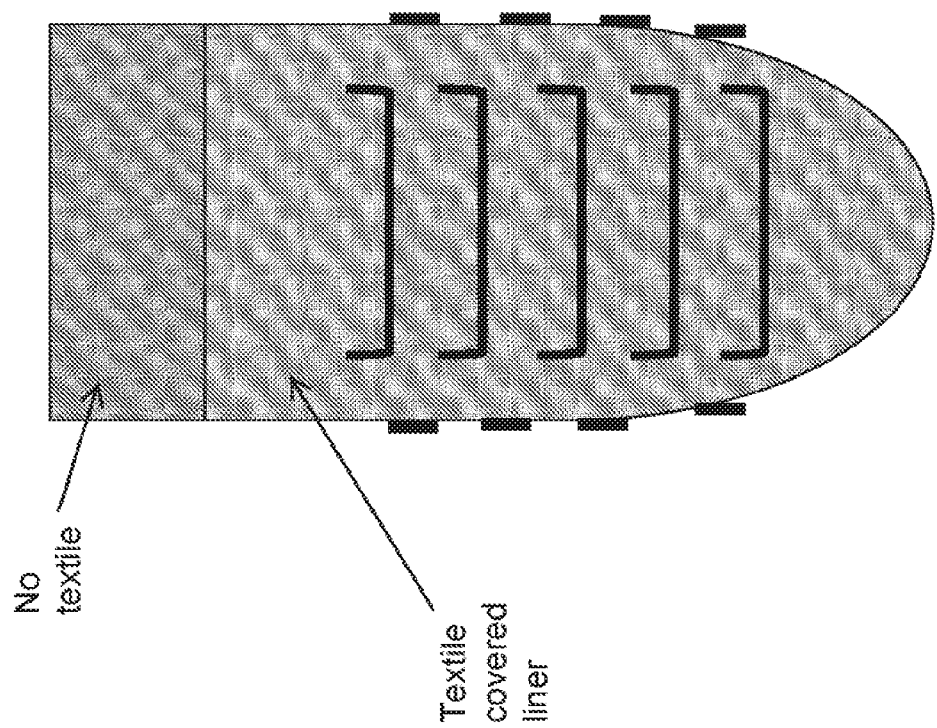
FIG. 3 provides a simplified front view of a second version of the liner apparatus shown in FIG. 1C having a textured, covered outer surface and raised grips in alternating patterns incorporated into the textile of the liner. A small portion of the liner at the top edge is not covered in textile to allow sealing with the socket.
Figure 4:
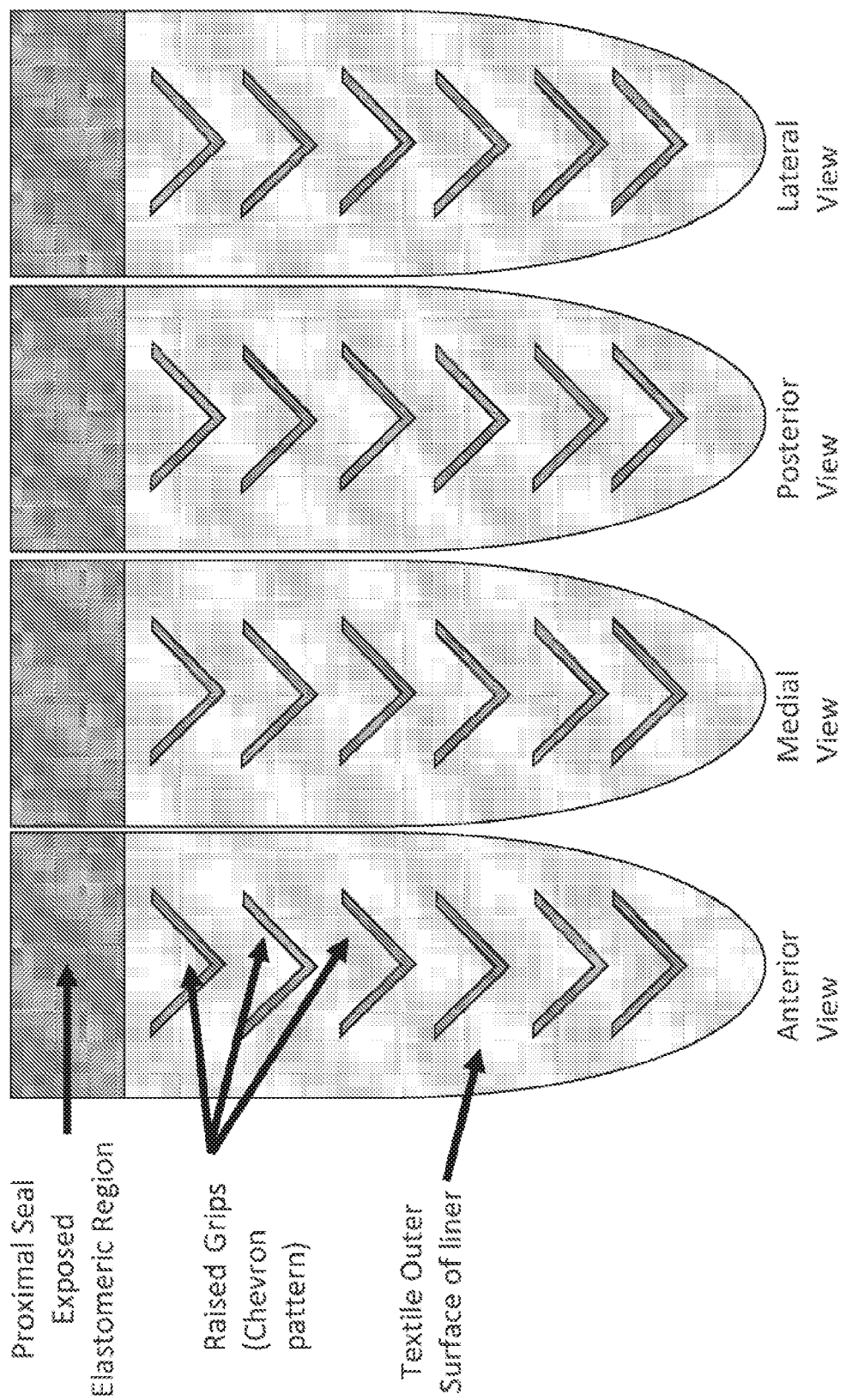
FIG. 4 provides simplified anterior, medial, posterior and lateral views of a liner apparatus of the second version depicted in FIGS. 1C and 3 having a different pattern for the raised grips.
Figure 5:
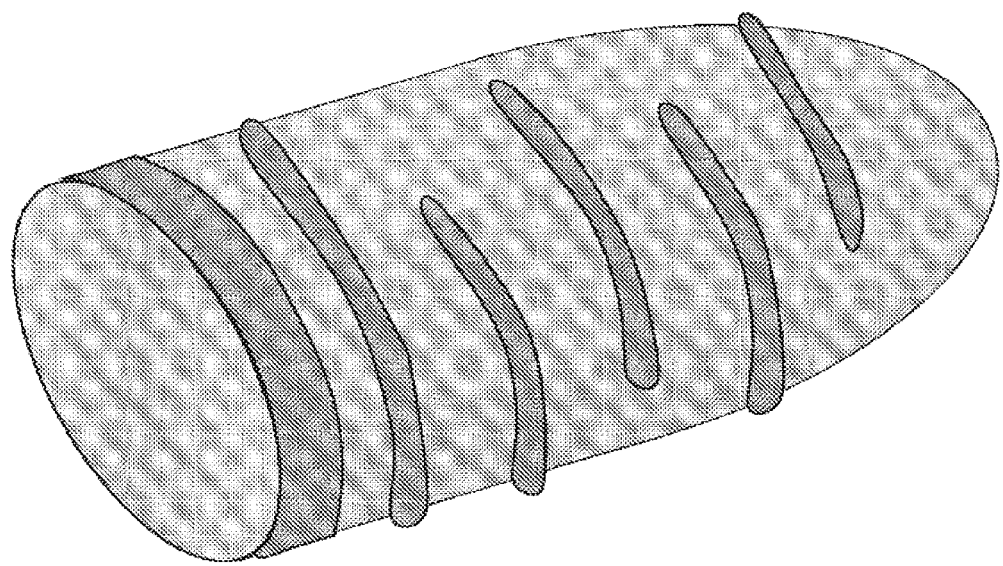
FIG. 5 provides a simplified perspective view of a liner apparatus of the second version depicted in FIGS. 1C and 3 having a further different raised grip pattern for the textile covered liner.

As seen in FIG. 1D and FIG. 2, an example of a first version of a liner apparatus includes a liner body having an outer surface and a plurality of intermittent and incomplete (discontinuous) raised elastomeric grips located on the outer surface of the liner body. In the context of this disclosure and all of the embodiments, "intermittent and incomplete" mean that the plurality of raised grips are discontinuous, such that they are spaced apart and do not entirely encircle the liner. As noted in FIGS. 1A-1D, the liner body may have a smooth or textured outer surface adjacent the raised grips, and the outer surface of the liner body includes at least an exposed smooth elastomeric region at the proximal end for sealing with the socket. FIG. 2 represents a first version having a liner body with a smooth outer surface, while FIGS. 3-5 represent different alternatives of a second version with a textile textured outer surface. Both constructions allow the suspension force to be located adjacent to the raised grips, which maximizes the liner's suspension and control of the socket.

The liner body and raised grips may be elastomeric and preferably are constructed of silicone, thermoplastic elastomer (TPE), polyurethane, or other suitable materials. To provide a textured outer surface of the liner body, as represented in the different alternatives of the second version in FIGS. 3-5, the liner body may include an imbedded textile or otherwise be formed so as to have a textured outer surface, which may otherwise be referred to herein as having a textile outer surface or as a textile covered liner. The raised grips on such liners may be integrally molded with the liner body, or laminated or adhered to the outer surface of the liner body. The raised grips may be formed in a Chevron pattern or any other pattern to secure the liner against the socket of the prosthesis. The external surface of the elastomeric liners with the elastomeric grips of the example first and second versions may provide unmatched rotation control. When the socket is subjected to passive suction or active vacuum, the raised elastomeric grips are held securely against the socket while the exposed smooth elastomeric region at the proximal end of the liner body seals to the socket. Indeed, when the socket is subjected to such passive suction or active vacuum, the air molecules may be removed below, above, and to either side of the raised grips, so as to hold the grips more securely to the inner wall of the socket, improving suspension.

Figure 6:
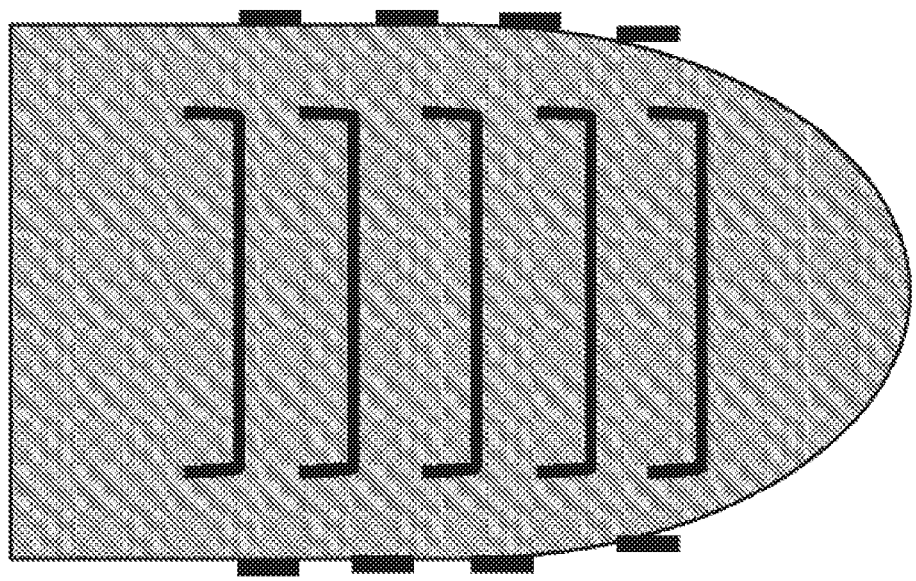
FIG. 6 provides a simplified front view of a third version which is provided as a stand-alone prosthetic sock having a textile sock portion covered by a membrane and having raised grips in alternating patterns on the inner and outer surfaces of the prosthetic sock, which is shown for example as part of the liner apparatus shown in FIGS. 1B and 1D, and may be used over any of the types of liners shown in FIGS. 2-5 or any standard liner.
Figure 7:
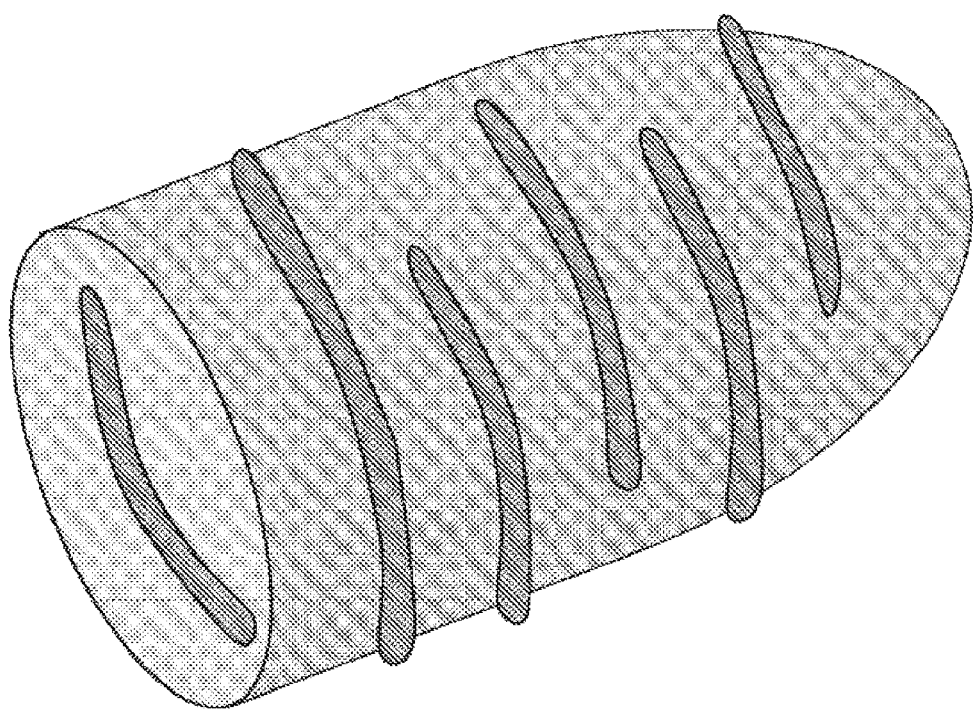
FIG. 7 provides a simplified perspective view of an alternative third version to that of FIG. 6 and which is shown as a prosthetic sock having a textile sock portion covered by a membrane and having raised grips on the inner and outer surfaces of the prosthetic sock.

To accommodate when a prosthesis user loses residual limb volume, a third version of the liner apparatus may further include a prosthetic sock having a textile sock portion, such as represented in FIGS. 1B and 1D, wherein example prosthetic socks are shown in FIGS. 6 and 7. The prosthetic socks shown in FIGS. 6 and 7 may be used over any of the example first or second versions of liners shown in FIGS. 2-5. Thus, an example third version of a liner apparatus is shown in FIGS. 6 and 7, and may be used as shown in FIGS. 1B and 1D.

Different ply thicknesses of the textile sock portion of FIGS. 6 and 7 may be used to accommodate lost volume of the residual limb. The prosthetic socks may have a similar elastomeric membrane and raised elastomeric grips on both the inner and outer surfaces of the textile sock portion to better hold against the outer surface of an underlying liner body and the inner wall of the socket of the prosthesis. The construction of the prosthetic socks may include similar materials to those of the liner apparatus of FIGS. 3-5. Thus, similar materials may be used and the raised grips on the prosthetic sock may be integrally molded with the membrane that covers the inner and outer surfaces of the textile sock portion, or may be laminated or otherwise adhered to the membrane that covers the inner and outer surfaces of the textile sock portion.

As shown in FIGS. 1B and 1D, the prosthetic socks of FIGS. 6 and 7 also may have a length that is shorter than the liner body, so that the prosthetic sock may be used in combination with one of the example first or second versions of liner bodies shown in FIGS. 2-5 to form a third example prosthetic liner apparatus wherein the sock does not cover the exposed smooth elastomeric region at the proximal end of the liner body for sealing with the socket. Alternatively, it will be appreciated that the prosthetic socks of FIGS. 6 and 7 may be used over a smooth or textured liner body that does not have intermittent and incomplete raised elastomeric grips located on the outer surface of the liner body and is constructed of materials similar to those described above with respect to the example first and second versions shown in FIGS. 2-5. It will be further appreciated that the raised grips may be formed in a Chevron pattern or any other pattern to secure the prosthetic sock against the surfaces of the liner and/or socket of the prosthesis.

Utilizing prosthetic socks with similar raised elastomeric grips as shown in FIGS. 1B, 1D, 6 and 7, but having different thicknesses of the textile sock portion and/or membrane, would allow the prosthetic user to maintain the enhanced coupling of the liner apparatus to the socket even as residual limb volume is changing.

It will be appreciated that a prosthetic liner apparatus for improving suspension and rotation control between a residual limb and a socket of a prosthesis in accordance with the present disclosure may be provided in various configurations. Any variety of suitable materials of construction, configurations, shapes and sizes for the components and methods of connecting the components may be utilized to meet the particular needs and requirements of an end user. It will be apparent to those skilled in the art that various modifications can be made in the design and construction of such prosthetic liner apparatus without departing from the scope or spirit of the claimed subject matter, and that the claims are not limited to the preferred embodiments illustrated herein.

What is claimed is:

1. A prosthetic liner apparatus for improving suspension and rotation control between a residual limb and a socket of a prosthesis, comprising:
    a liner body having a shape configured to receive the residual limb and having an outer surface that fits within the socket;
    a plurality of intermittent and incomplete raised elastomeric grips located on the outer surface of the liner body;
    wherein at a proximal end of the liner body, the outer surface of the liner body includes at least an exposed smooth elastomeric region that fits within and seals with the socket;
    wherein when the socket is subjected to passive suction or active vacuum, the raised elastomeric grips are held securely against the socket while the exposed smooth elastomeric region at the proximal end of the liner body seals to the socket; and
    wherein the plurality of intermittent and incomplete raised elastomeric grips form a chevron pattern.

2. The prosthetic liner apparatus of claim 1 wherein the raised elastomeric grips are laminated or adhered to the outer surface of the liner body.

3. The prosthetic liner apparatus of claim 1 wherein the raised elastomeric grips are integrally formed with the liner body.

4. The prosthetic liner apparatus of claim 1 wherein the liner body has a smooth outer surface.

5. The prosthetic liner apparatus of claim 1 wherein the liner body has a textured outer surface below the smooth elastomeric region at the proximal end of the liner body.

6. The prosthetic liner apparatus of claim 1 wherein when the socket is subjected to passive suction or active vacuum, air molecules are removed below, above and to the sides of the raised elastomeric grips, so as to hold the raised elastomeric grips securely to the socket while the smooth elastomeric region at the proximal end of the liner body seals to the socket.

7. The prosthetic liner apparatus of claim 1 wherein the liner body is constructed of silicone, thermoplastic elastomer (TPE), or polyurethane.

8. The prosthetic liner apparatus of claim 1 further comprising a prosthetic sock having a textile sock portion having inner and outer surfaces covered by an elastomeric membrane and being configured to receive the liner body and to have the outer surface of the prosthetic sock fit within the socket, and having a plurality of intermittent and incomplete raised elastomeric grips located on the elastomeric membrane that covers the inner and outer surfaces of the textile sock portion, so as to extend inward and outward from the prosthetic sock.

9. The prosthetic liner apparatus of claim 8 wherein the raised elastomeric grips on the elastomeric membrane that covers the inner and outer surfaces of the textile sock portion are laminated or adhered to the elastomeric membrane.

10. The prosthetic liner apparatus of claim 8 wherein the raised elastomeric grips on the elastomeric membrane that covers the inner and outer surfaces of the textile sock portion are integrally formed with the membrane.

11. The prosthetic liner apparatus of claim 8 wherein the prosthetic sock does not cover the exposed smooth elastomeric region at the proximal end of the liner body when the liner body is received in the prosthetic sock.

12. A prosthetic liner apparatus for improving suspension and rotation control between a residual limb and a socket of a prosthesis, comprising:
    a liner body having a shape configured to receive the residual limb and having an outer surface that fits within the socket; wherein at a proximal end of the liner body, the outer surface of the liner body includes at least an exposed smooth elastomeric region that fits within and seals with the socket;
    a prosthetic sock having a textile sock portion having inner and outer surfaces covered by an elastomeric membrane and being configured to receive the liner body and to have the outer surface of the prosthetic sock fit within the socket, and having a plurality of intermittent and incomplete raised elastomeric grips located on the elastomeric membrane that covers the inner and outer surfaces of the textile sock portion, so as to extend inward and outward from the prosthetic sock;

wherein when the socket is subjected to passive suction or active vacuum, the raised elastomeric grips are held securely against the socket; and wherein the plurality of intermittent and incomplete raised elastomeric grips form a chevron pattern.

13. The prosthetic liner apparatus of claim 12 wherein the liner body has a smooth or textured outer surface.

14. The prosthetic liner apparatus of claim 12 wherein a plurality of intermittent and incomplete raised elastomeric grips are located on the outer surface of the liner body.

15. The prosthetic liner apparatus of claim 12 wherein the raised elastomeric grips on the elastomeric membrane that covers the inner and outer surfaces of the textile sock portion are laminated or adhered to the elastomeric membrane.

16. The prosthetic liner apparatus of claim 12 wherein the raised elastomeric grips on the elastomeric membrane that covers the inner and outer surfaces of the textile sock portion are integrally formed with the membrane.

17. The prosthetic liner apparatus of claim 12 wherein at a proximal end of the liner body, the outer surface of the liner body includes at least an exposed smooth elastomeric region that fits within and seals with the socket, and the prosthetic sock does not cover the exposed smooth elastomeric region at the proximal end of the liner body when the liner body is received in the prosthetic sock.

18. The prosthetic liner apparatus of claim 12 wherein the raised elastomeric grips on the elastomeric membrane that covers the inner and outer surfaces of the textile sock portion are constructed of silicone, thermoplastic elastomer (TPE), or polyurethane.

19. A prosthetic liner apparatus for improving suspension and rotation control between a residual limb and a socket of a prosthesis, comprising:
  a liner body having a shape configured to receive the residual limb and having an outer surface that fits within the socket;
  a plurality of intermittent and incomplete raised elastomeric grips located on the outer surface of the liner body;
  wherein at a proximal end of the liner body, the outer surface of the liner body includes at least an exposed smooth elastomeric region that fits within and seals with the socket; and
  wherein the plurality of intermittent and incomplete raised elastomeric grips form a chevron pattern.

20. The prosthetic liner apparatus of claim 19 wherein the liner body has a textured outer surface below a smooth elastomeric region at the proximal end of the liner body.

* * * * *